United States Patent [19]

Takatsu et al.

[11] Patent Number: 4,726,910
[45] Date of Patent: Feb. 23, 1988

[54] TOLAN-TYPE NEMATIC LIQUID CRYSTALLINE COMPOUNDS

[75] Inventors: Haruyoshi Takatsu, Kodaira; Makoto Sasaki, Urawa; Yasuyuki Tanaka; Hisato Sato, both of Tokyo, all of Japan

[73] Assignee: Dainippon Ink and Chemicals, Inc., Tokyo, Japan

[21] Appl. No.: 42,524

[22] Filed: Apr. 27, 1987

Related U.S. Application Data

[63] Continuation of Ser. No. 692,570, Jan. 18, 1985, abandoned.

[30] Foreign Application Priority Data

| Jan. 23, 1984 | [JP] | Japan | 59-8519 |
|---|---|---|---|
| Jan. 24, 1984 | [JP] | Japan | 59-10658 |
| Mar. 29, 1984 | [JP] | Japan | 59-58588 |
| Mar. 29, 1984 | [JP] | Japan | 59-58589 |
| Jun. 19, 1984 | [JP] | Japan | 59-124489 |
| Dec. 11, 1984 | [JP] | Japan | 59-261413 |
| Dec. 11, 1984 | [JP] | Japan | 59-261413 |

[51] Int. Cl.$^4$ .................. C09K 19/54; C09K 19/06; C09K 19/30; C09K 19/34
[52] U.S. Cl. .................. 252/299.5; 252/299.6; 252/299.61; 252/299.63; 252/299.65; 252/299.67; 252/299.66; 252/299.64
[58] Field of Search ............ 252/299.5, 299.6, 299.61, 252/299.63, 299.65, 299.66, 299.67, 299.64; 585/25

[56] References Cited

U.S. PATENT DOCUMENTS

| 3,925,482 | 12/1975 | Jacques | 252/299.6 |
|---|---|---|---|
| 4,181,625 | 1/1980 | Eidenschink et al. | 252/299.63 |
| 4,229,315 | 10/1980 | Krause et al. | 252/299.63 |
| 4,253,740 | 3/1981 | Raynes et al. | 350/350 R |
| 4,331,552 | 5/1982 | Eidenschink et al. | 252/299.6 |
| 4,410,283 | 10/1983 | Dubois et al. | 252/299.64 |
| 4,551,264 | 11/1985 | Eidenschink et al. | 252/299.61 |
| 4,564,694 | 1/1986 | Hirai et al. | 252/299.63 |
| 4,670,182 | 6/1987 | Fujita et al. | 252/299.61 |

FOREIGN PATENT DOCUMENTS

| 58981 | 9/1982 | European Pat. Off. | 252/299.6 |
|---|---|---|---|
| 2309501 | 9/1973 | Fed. Rep. of Germany | 252/299.6 |
| 2645518 | 4/1978 | Fed. Rep. of Germany | 252/299.6 |
| 2644219 | 4/1978 | Fed. Rep. of Germany | 252/299.6 |
| 56-123903 | 9/1981 | Japan | 585/25 |

OTHER PUBLICATIONS

Cox et al., Mol. Cryst. Liq. Cryst., vol. 37, pp. 241-248 (1976).

(List continued on next page.)

Primary Examiner—Teddy S. Gron
Assistant Examiner—J. E. Thomas
Attorney, Agent, or Firm—Sherman and Shalloway

[57] ABSTRACT

A liquid crystalline compound of the general formula

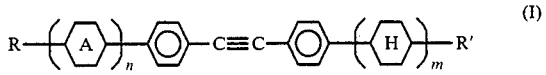

wherein

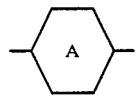

represents

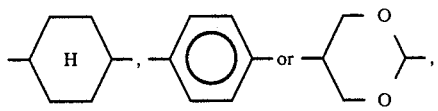

R and R', independently from each other, represent a linear alkyl group having 1 to 10 carbon atoms, an alkoxymethylene group whose alkoxy moiety has 1 to 10 carbon atoms, a cyano group or a halogen atom, and n and m, independently from each other, represent 0 or 1.

6 Claims, 9 Drawing Figures

OTHER PUBLICATIONS

Flussige Kristalle in Tabellen, Demus et al., pp. 52–55 (1976).
Gray et al., Mol. Cryst. Liq. Cryst., vol. 37, pp. 213–231 (1976).
Malthete et al., Mol. Cryst. Liq. Cryst., vol. 23, pp. 233–260 (1973).
Dubois et al., Mol. Cryst. Liq. Cryst., vol. 27, pp. 187–198 (1974).
Adomenas et al., Advances LC Research & Appl., vol. 2, pp. 1029–1038 (1980).
Flussige Kristalle in Tabellen II, Demus et al., p. 104, (1984).
Han et al., J. Organic Chemistry, vol. 46, pp. 4695–4700 (1981).
Praefcke et al., Chemiker Zeitung, pp. 269–271, Sep. 1980.

TOLAN-TYPE NEMATIC LIQUID CRYSTALLINE COMPOUNDS

This application is a continuation of application Ser. No. 692,570, filed Jan. 18, 1985, now abandoned.

This invention relates to novel tolan derivatives useful as an electrooptical display material. The novel tolan derivatives provided by this invention are compounds of the general formula

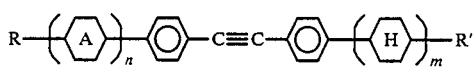

wherein

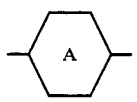

represents

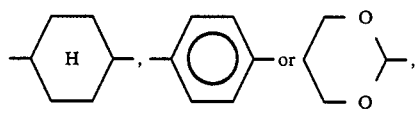

R and R', independently from each other, represent a linear alkyl group having 1 to 10 carbon atoms, an alkoxymethylene group whose alkoxy moiety has 1 to 10 carbon atoms, a cyano group or a halogen atom, and n and m, independently from each other, represent 0 or 1 and are referred to hereinafter as the compounds of formula (I).

Typical liquid crystal display cells include a field effect mode cell proposed by M. Schadt et al. [APPLIED PHYSICS LETTERS, 18, 127–128 (1971)], a dynamic scattering mode cell proposed by G. H. Heilmeier et al. [PROCEEDINGS OF THE I.E.E.E., 56, 1162–1171 (1968)], and a guest-host mode cell proposed by G. H. Heilmeier et al. [APPLIED PHYSICS LETTERS, 13, 91 (1968)] or D. L. White et al. [JOURNAL OF APPLIED PHYSICS, 45, 4718 (1974)].

Among these liquid crystalline cells, a TN-type cell, a kind of the field effect mode cell, is now most prevailing. As reported by G. Bauer in Mol. Cryst. Liq. Cryst., 63, 45 (1981), the product of the thickness (d in micrometers) of the TN-type cell multiplied by the anisotropy ($\Delta n$) of the refractive index of a liquid crystalline material filled in the cell should be preset at a specified value in order to prevent the occurrence of interference fringes on the cell surface which impair the appearance of the cell. In liquid crystalline cells now in practical use, the $\Delta n \times d$ value is set at one of 0.5, 1.0, 1.6 and 2.2. Hence, the d value can be decreased if a liquid crystalline material having a large $\Delta n$ value is used. If the d value becomes smaller, the response time ($\tau$) becomes shorter in accordance with the well-known expression $\gamma \alpha d^2$. Accordingly, liquid crystalline materials having large $\Delta n$ values are very important for the production of liquid crystal display cells having a high response speed and being free from interference fringes.

The response time ($\tau$) is proportional to the viscosity ($\eta$) of a liquid crsytalline material (namely, $\tau \alpha \eta$). In other words, liquid crystalline materials having large $\Delta n$ values and low viscosities are very important for the production of fast-responsive liquid crystal display cells.

The compounds represented by the formula

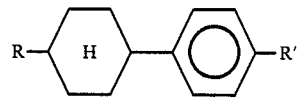

or

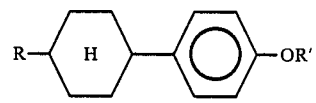

(wherein R and R' represent a linear alkyl group) described in U.S. Pat. No. 4,130,502 are especially good viscosity reducing agents for use in the production of fast-responsive liquid crystal display cells. These compounds can reduce the viscosity of mixed liquid crystals, but have the defect of decreasing their $\Delta n$ values.

Many of practical liquid crystalline materials are prepared by mixing compounds having a nematic phase at room temperature or in its vicinity with compounds having a nematic phase at temperatures higher than room temperature. Many mixed liquid crystals of the above type now in practical use are required to have a nematic phase at least over the entire range of $-30°$ C. to $+65°$ C. As the range of application of liquid crystal display cells has become wider, it has been desired to obtain liquid crystalline materials having a nematic liquid crystalline temperature range broadened to still higher temperatures. For this reason, a particular need has arisen recently for nematic liquid crystalline compounds having a high nematic phase-isotropic liquid phase transition temperature (this temperature is referred to as the N-I point). U.S. Pat. Nos. 4,229,315 and 4,331,552 and West German Laid-Open Patent Publication No. 3233641 describe typical nematic liquid crystalline compounds having high N-I points which, however, have low $\Delta n$ values.

The compounds of formula (I) in accordance with this invention are novel tolan derivatives all of which commonly have large $\Delta n$ values, some of which have high N-I points, and some of which have an excellent ability to reduce viscosity.

Most of the compounds of formula (I) are nematic liquid crystalline compounds. Some of them are not liquid-crystalline, but are useful as viscosity reducing agents for liquid crystals. Accordingly, practical mixed liquid crystalline materials having a large $\Delta n$ value, a high N-I point and a low viscosity can be prepared by mixing various matrix liquid crystals with the compounds of formula (I).

Figure 1:
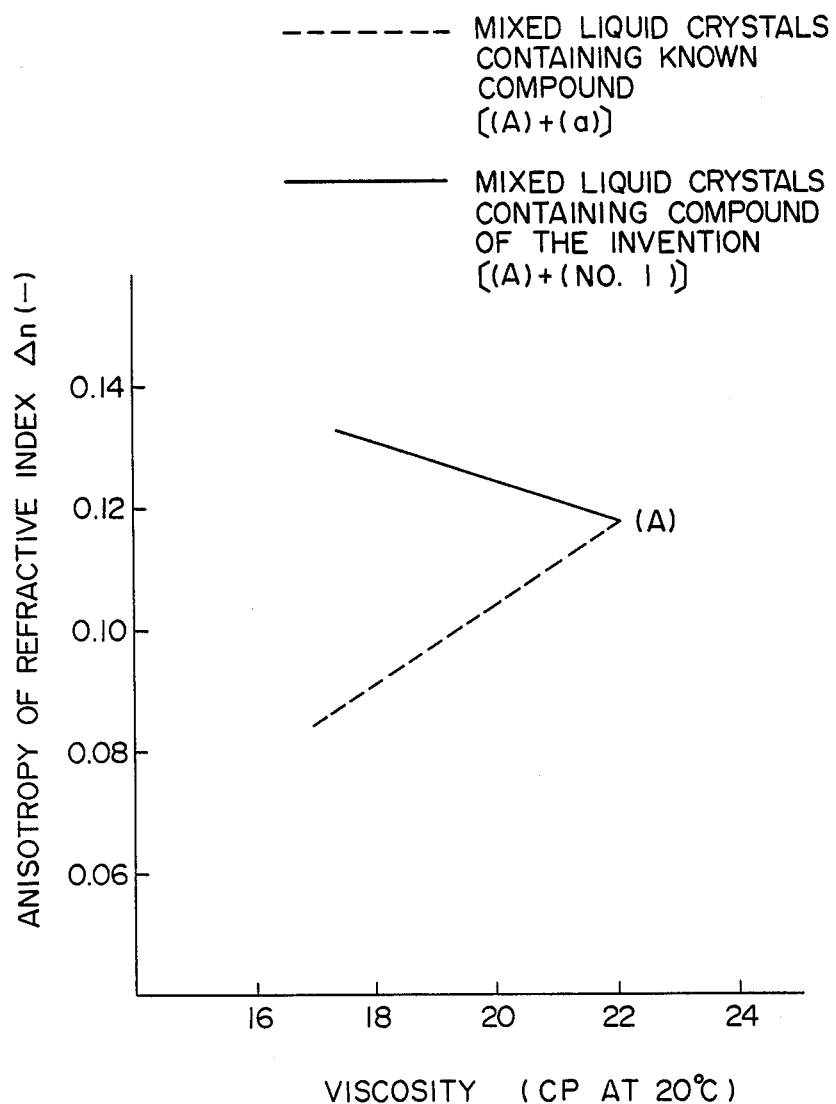
FIG. 1 is a graph showing the relationship between viscosity and $\Delta n$ values for a mixed liquid crystal composition according to this invention and a comparative composition.
Figure 2:
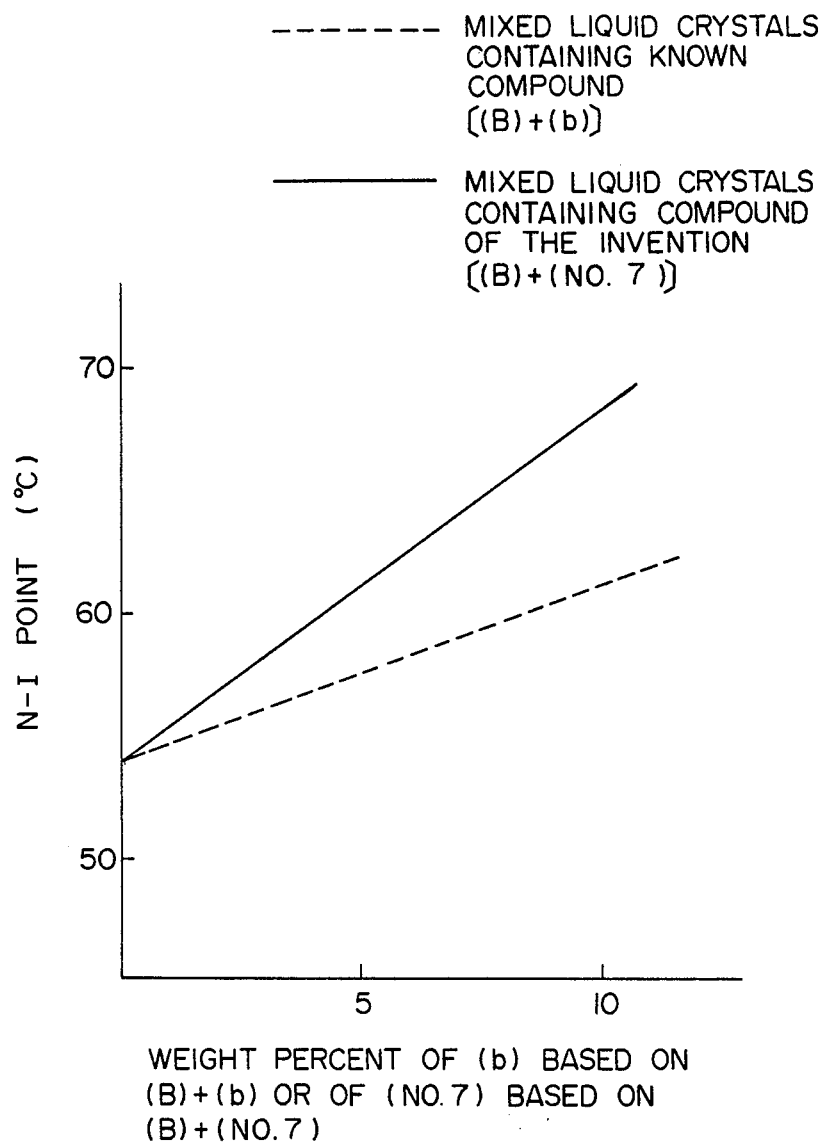
FIGS. 2, 4, 6 and 8 are graphs showing the relationship between the N-I points and amount of invention or conventional additive compound.
Figure 3:
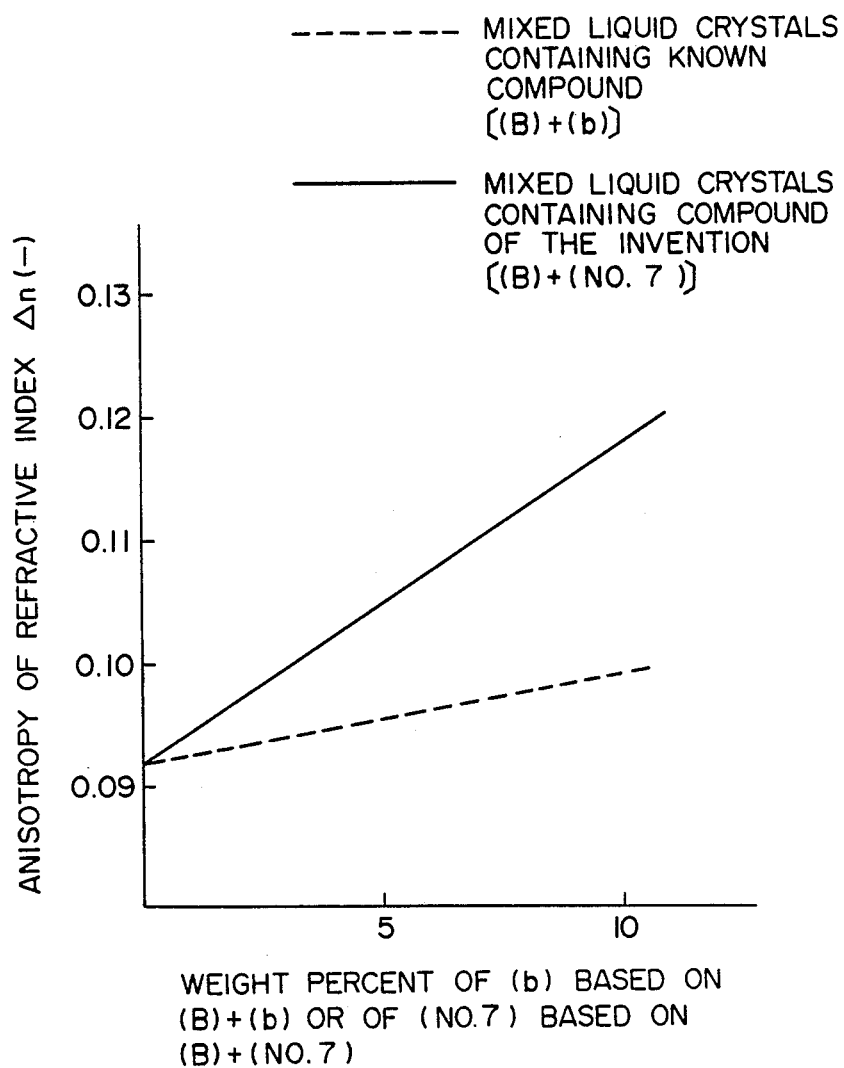
FIGS. 3, 5, 7 and 9 are graphs showing the relationship between the $\Delta n$ values and amount of invention or conventional additive compound.
Figure 4:
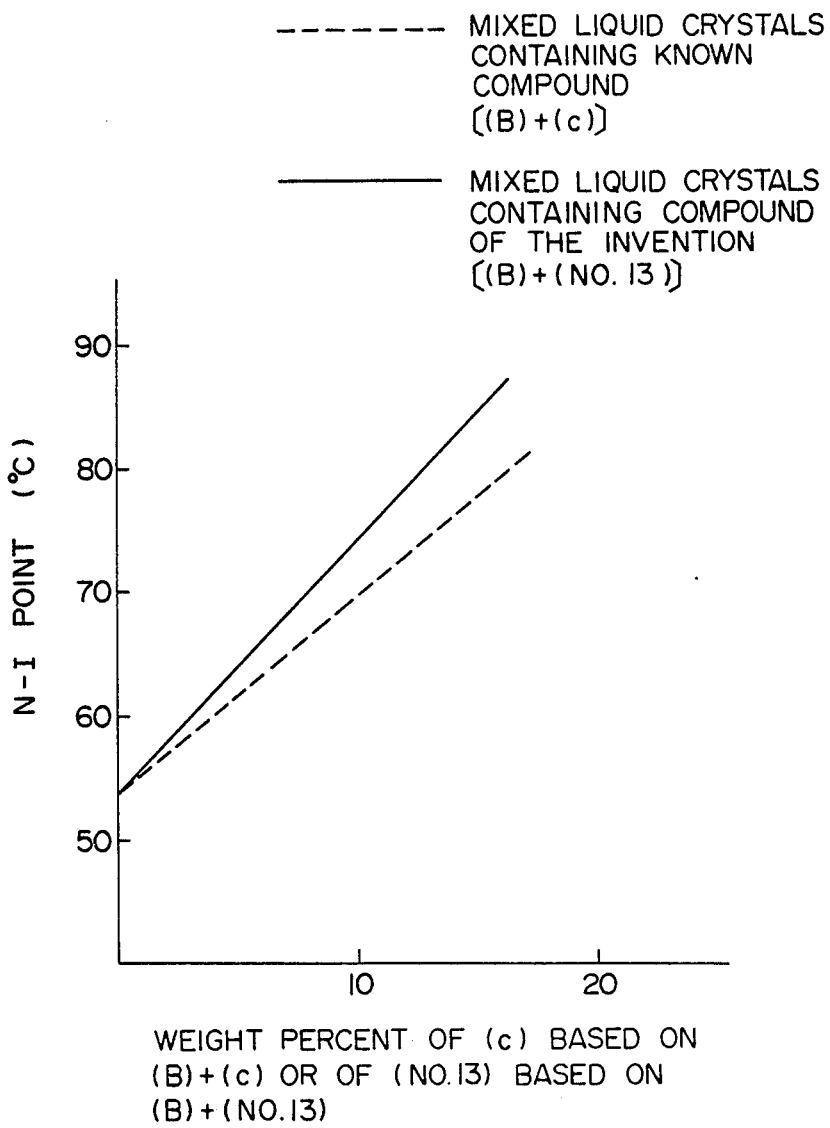
Figure 5:
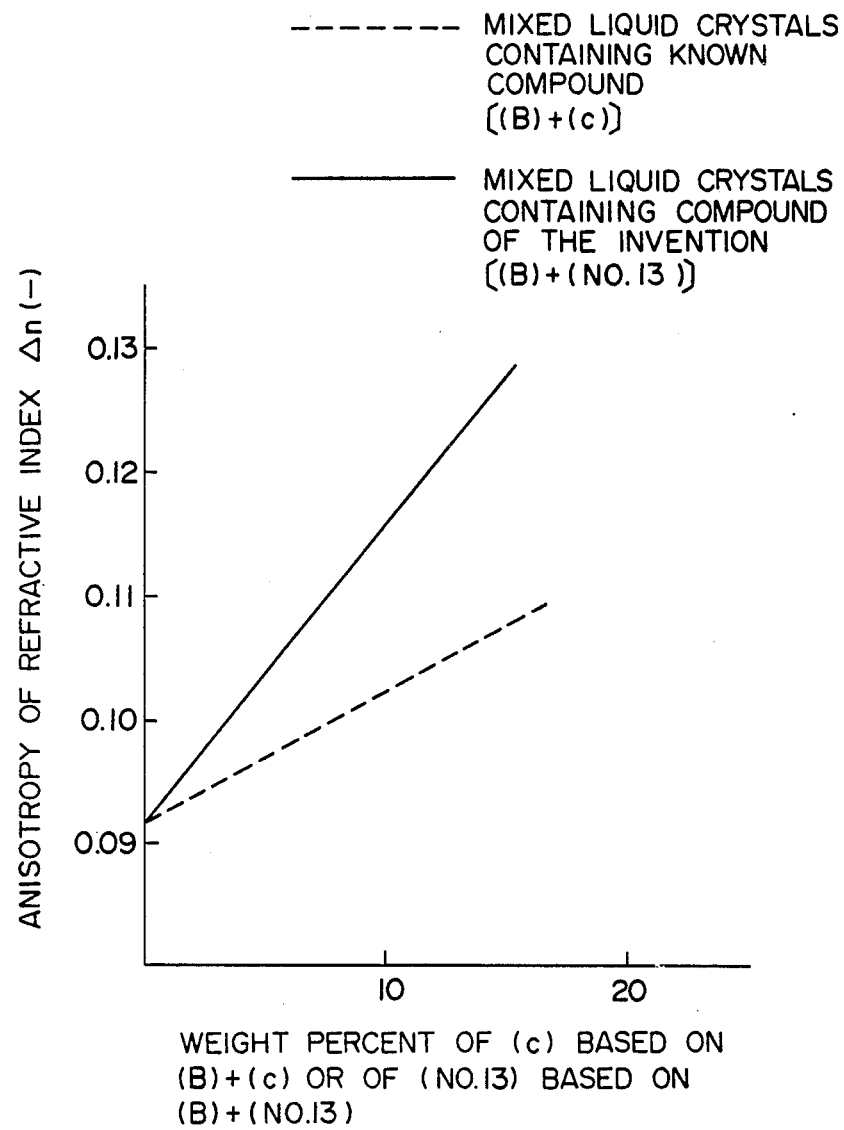
Figure 6:
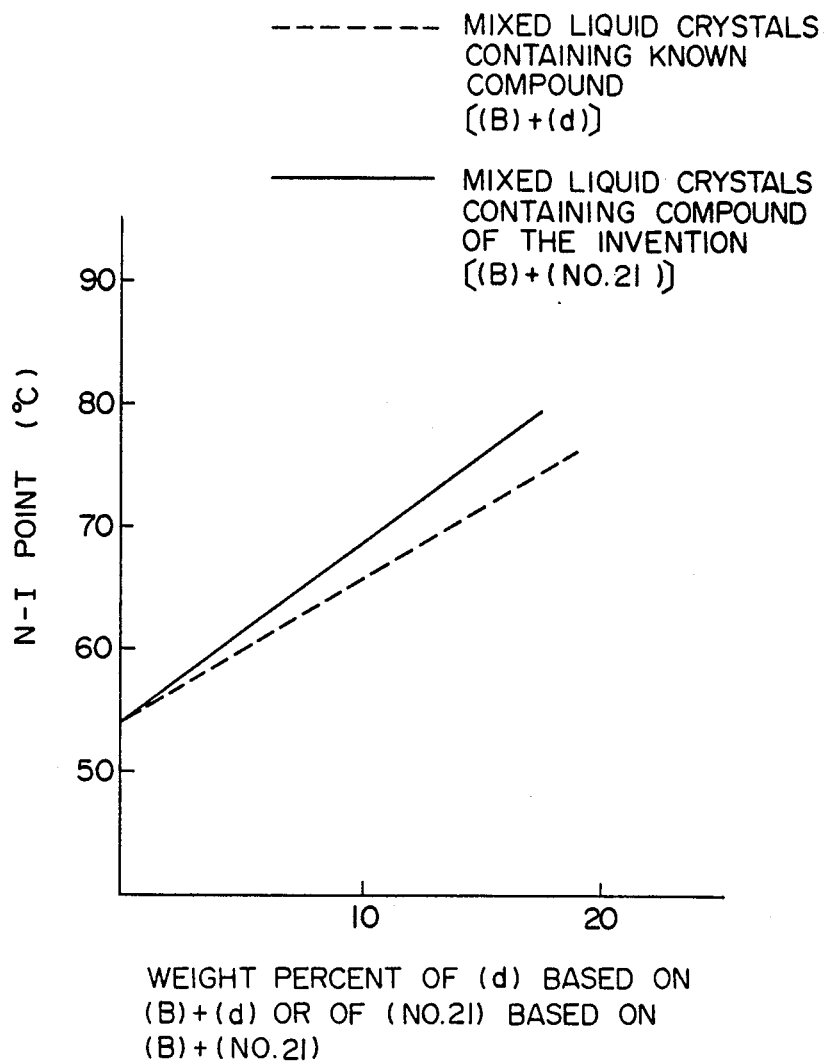
Figure 7:
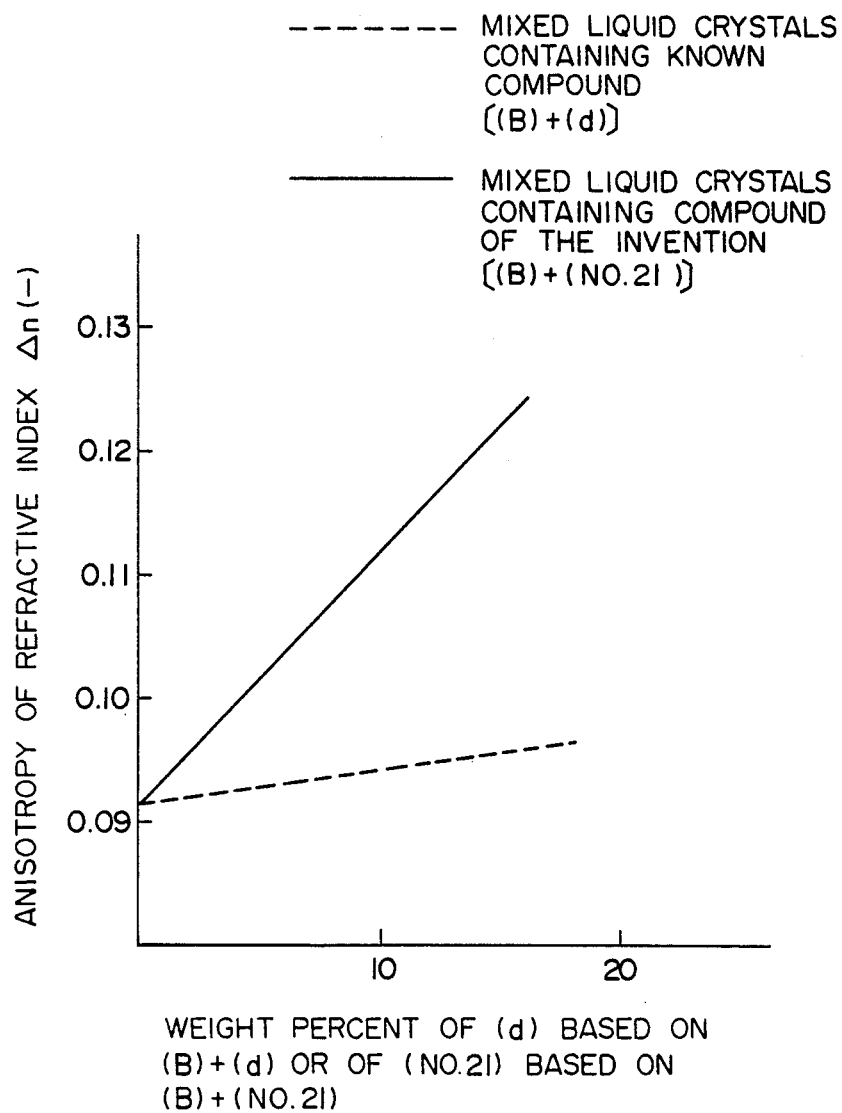
Figure 8:
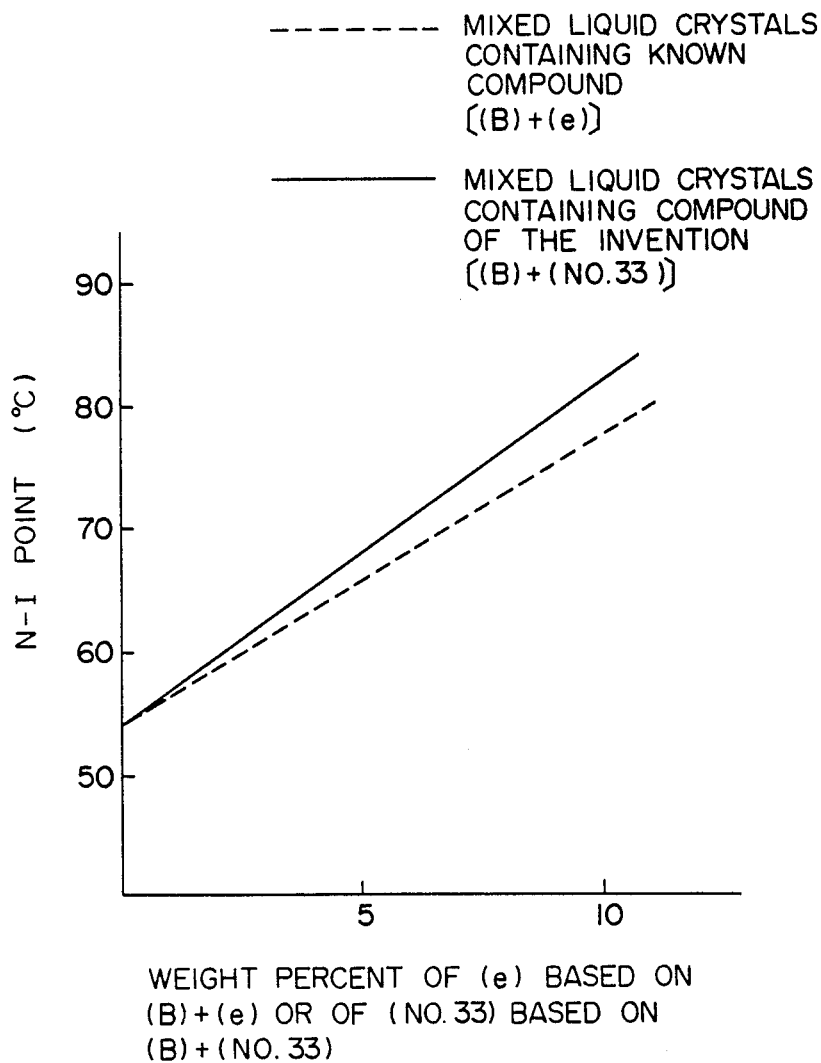
Figure 9:
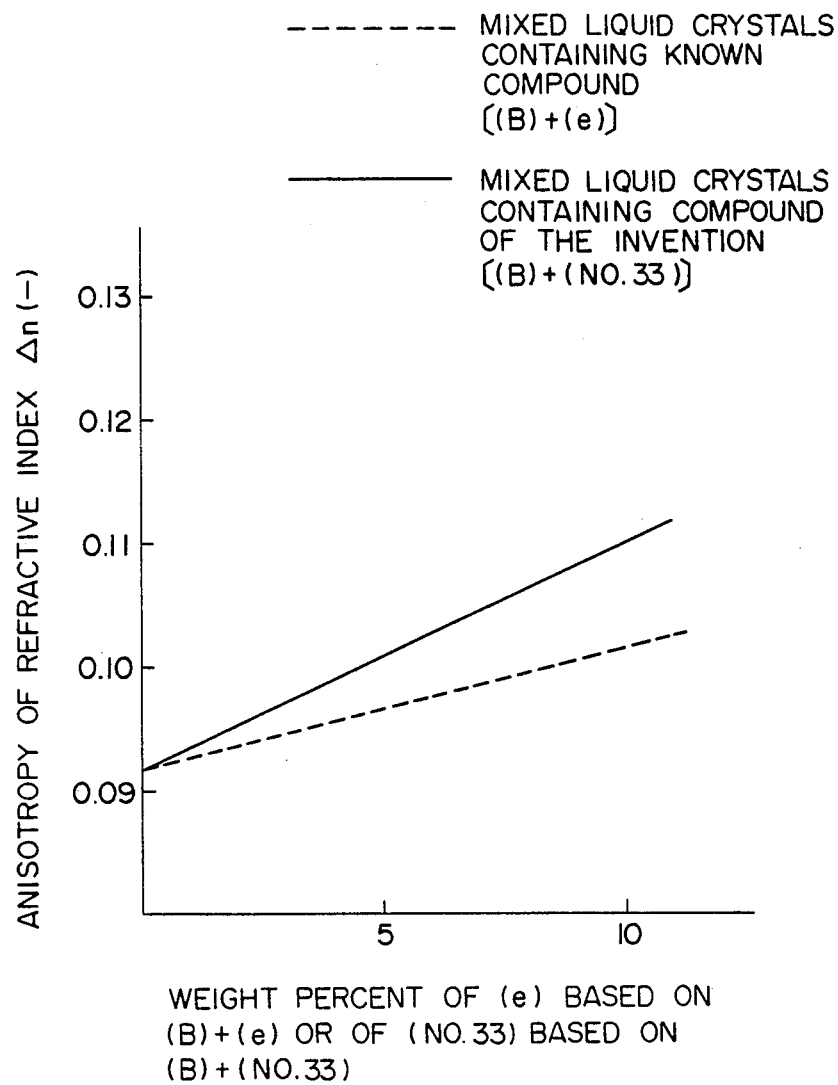

The compounds of formula (I) can be produced by the following process. This process, however, is not applicable to the production of compounds of general formula (I) in which

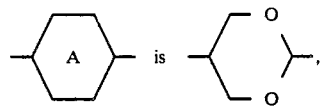

and compounds of general formula (I) in which R or R' is an alkoxymethylene group.

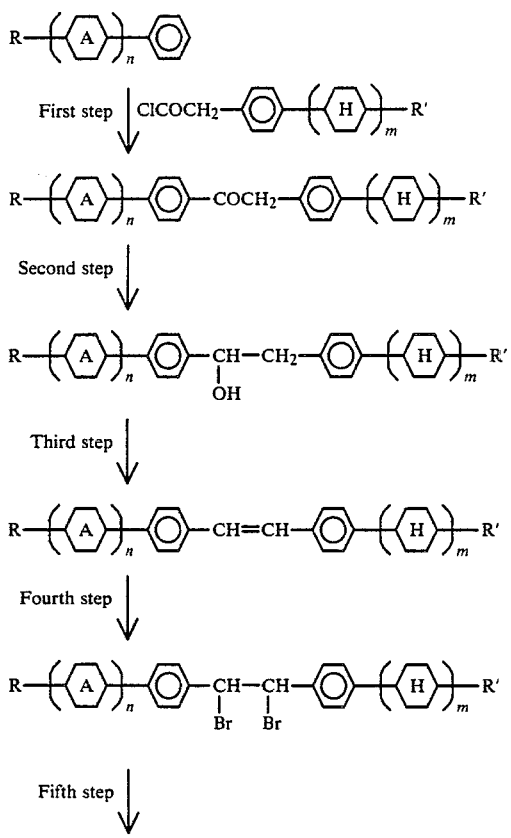

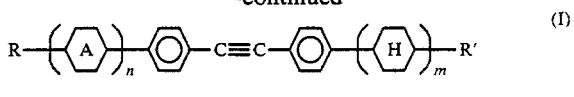

First step
The compound of formula (i) is reacted with the compound of formula (ii) and anhydrous aluminum chloride in carbon disulfide or nitrobenzene to produce the compound of formula (iii).

Second step
The compound of formula (iii) produced in the first step is reacted with a reducing agent such as lithium aluminum hydride in anhydrous ether or anhydrous tetrahydrofuran to produce the compound of formula (iv).

Third step
A dehydrating agent such as potassium hydrogen sulfate is added to the compound of formula (iv) produced in the second step, and the mixture is heated to perform dehydration and to produce the compound of formula (v).

Fourth step
The compound of formula (v) produced in the third step is reacted with bromine in a solvent such as carbon tetrachloride, chloroform or 1,1,2-trichloroethane to produce the compound of formula (vi).

Fifth step
The compound of formula (vi) produced in the fourth step is reacted with a base such as 1,5-diazabicyclo[5.4.0]undecene-5 in a solvent such as N,N-dimethylformamide to produce the compound of formula (I).

The compound of formula (I) in which R or R' is CN can also be produced by first preparing the compound of formula (I) in which R or R' is Br and reacting the resulting compound with cuprous cyanide in a solvent such as N,N-dimethylformamide.

The compounds of formula (I) in which

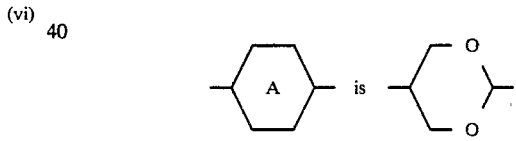

can be produced by the following process.

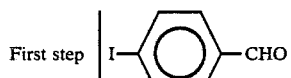

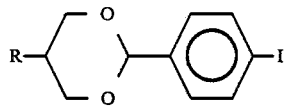

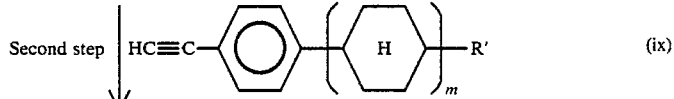

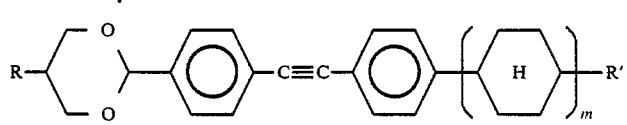

In the first step, the compound of formula (vii) is reacted with p-iodobenzaldehyde in a solvent such as toluene to produce the compound of formula (viii). In the second step, the compound of formula (viii) produced in the first step is reacted with the compound of formula (ix) in a solvent such as N,N-dimethylformamide in the presence of a catalyst such as bis(triphenylphosphine)palladium (II) chloride to give the compound of formula (I).

The compounds of general formula (I) in which R or R' is an alkoxymethylene group can be produced by the following process.

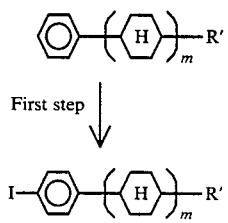

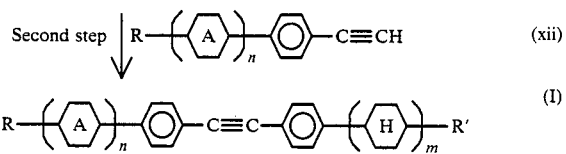

In the first step, the compound of formula (x) is reacted with iodine in a mixed solvent of acetic acid and water to produce the compound of formula (xi). In the second step, the compound of formula (xi) produced in the first step is reacted with the compound of formula (xii) in a solvent such as N,N-dimethylformamide in the presence of a catalyst such as bis(triphenylphosphine)palladium (II) chloride to give the compound of formula (I).

Table 1 summarizes the transition temperatures of the compounds of formula (I) produced as above. In Table 1, all cyclohexane rings have a trans(equatorial-equatorial) configuration, and C, N, and I stand for a crystalline phase, a nematic phase and an isotropic liquid phase, respectively.

TABLE 1

| No. | R | ⟨A⟩ₙ | m | R' | Transition temperature (°C.) | |
|---|---|---|---|---|---|---|
| 1 | n-C₃H₇— | — | 0 | C₂H₅ | 51 (C →I) | |
| 2 | n-C₃H₇— | — | 0 | n-C₃H₇— | 73 (C →I) | |
| 3 | n-C₃H₇— | — | 0 | n-C₄H₉— | 22 (C →I) | 15 (I ⇌ N) |
| 4 | n-C₄H₉ | — | 0 | n-C₄H₉ | 41 (C →I) | |
| 5 | n-C₄H₉ | — | 0 | n-C₅H₁₁ | 26 (C →I) | 21 (I ⇌ N) |
| 6 | F | ⟨phenyl⟩ | 0 | C₂H₅— | 159 (C →N) | 193 (N ⇌ I) |
| 7 | F | ⟨phenyl⟩ | 0 | n-C₃H₇— | 162 (C →N) | 202 (N ⇌ I) |
| 8 | F | ⟨phenyl⟩ | 0 | n-C₅H₁₁— | 165 (C →N) | 204 (N ⇌ I) |
| 9 | Cl | ⟨phenyl⟩ | 0 | n-C₃H₇— | 188 (C →N) | 230 (N ⇌ I) |

TABLE 1-continued
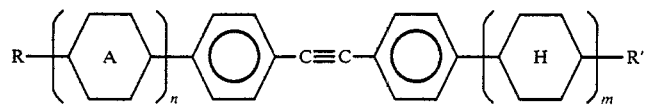
(I)
| No. | R | (A)ₙ | m | R' | Transition temperature (°C.) | |
|---|---|---|---|---|---|---|
| 10 | C₂H₅— |  | 0 | F | 150 (C ⟶ N) | 196 (N ⇌ I) |
| 11 | n-C₃H₇— | 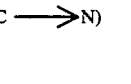 | 0 | F | 154 (C ⟶ N) | 207 (N ⇌ I) |
| 12 | n-C₃H₇— |  | 0 | —Br | 155 (C ⟶ N) | 221 (N ⇌ I) |
| 13 | n-C₃H₇— | 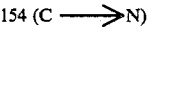 | 0 | —CN | 153 (C ⟶ N) | 265 (N ⇌ I) |
| 14 | n-C₃H₇— | 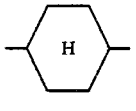 | 0 | —Cl | 141 (C ⟶ N) | 219 (N ⇌ I) |
| 15 | n-C₃H₇— |  | 0 | —F | 90 (C ⟶ N) | 189 (N ⇌ I) |
| 16 | C₂H₅ | 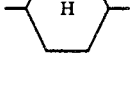 | 0 | —CN | 135 (C ⟶ N) | 250 (N ⇌ I) |
| 17 | C₂H₅ |  | 0 | —Br | 136 (C ⟶ N) | 209 (N ⇌ I) |
| 18 | C₂H₅ |  | 0 | —Cl | 124 (C ⟶ N) | 207 (N ⇌ I) |
| 19 | C₂H₅ |  | 0 | —F | 78 (C ⟶ N) | 179 (N ⇌ I) |
| 20 | C₂H₅— | 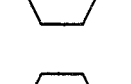 | 0 | n-C₃H₇— | 86 (C ⟶ N) | 189 (N ⇌ I) |

TABLE 1-continued $$R \left( \boxed{A} \right)_n \boxed{\phantom{O}} - C \equiv C - \boxed{\phantom{O}} \left( \boxed{H} \right)_m R' \quad (I)$$

| No. | R | $\left(\boxed{A}\right)_n$ | m | R' | Transition temperature (°C.) | |
|-----|---|---|---|----|------|------|
| 21 | n-C$_3$H$_7$— | ⬡H | 0 | n-C$_3$H$_7$— | 96 (C⟶N) | 213 (N⇌I) |
| 22 | n-C$_3$H$_7$— | ⬡H | 0 | n-C$_4$H$_9$— | 87 (C⟶N) | 201 (N⇌I) |
| 23 | n-C$_3$H$_7$— | ⬡H | 0 | n-C$_5$H$_{11}$— | 98 (C⟶N) | 209 (N⇌I) |
| 24 | n-C$_4$H$_9$— | ⬡H | 0 | n-C$_3$H$_7$— | 89 (C⟶N) | 207 (N⇌I) |
| 25 | n-C$_5$H$_{11}$— | ⬡H | 0 | C$_2$H$_5$— | 91 (C⟶N) | 192 (N⇌I) |
| 26 | C$_2$H$_5$— | ⬡ | 0 | n-C$_3$H$_7$— | 163 (C⟶N) | 221 (N⇌I) |
| 27 | n-C$_3$H$_7$— | ⬡ | 0 | n-C$_3$H$_7$— | 164 (C⟶N) | 230 (N⇌I) |
| 28 | n-C$_5$H$_{11}$— | ⬡ | 0 | n-C$_3$H$_7$— | 160 (C⟶N) | 211 (N⇌I) |
| 29 | n-C$_5$H$_{11}$— | ⬡ | 0 | C$_2$H$_5$— | 157 (C⟶N) | 206 (N⇌I) |
| 30 | C$_2$H$_5$— | ⬡H | 1 | n-C$_3$H$_7$— | 194 (C⟶N) | above 300 (N⇌I) |
| 31 | C$_2$H$_5$— | ⬡H | 1 | n-C$_5$H$_{11}$— | 210 (C⟶N) | above 300 (N⇌I) |

TABLE 1-continued

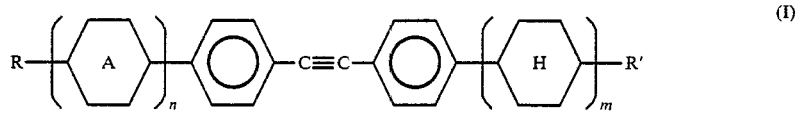

| No. | R | {A}ₙ | m | R' | Transition temperature (°C.) | |
|---|---|---|---|---|---|---|
| 32 | n-C₃H₇— | -{H}- | 1 | n-C₃H₇— | 185 (C⟶N) | above 300 (N⇌I) |
| 33 | n-C₃H₇— | -{H}- | 1 | n-C₅H₁₁— | 202 (C⟶N) | above 300 (N⇌I) |
| 34 | n-C₃H₇ | -{O...O}- | 0 | n-C₄H₉ | 83 (C⟶N) | 195 (N⇌I) |
| 35 | n-C₃H₇ | -{O...O}- | 0 | F | 118 (C⟶N) | 178 (N⇌I) |
| 36 | n-C₆H₁₃ | -{O...O}- | 0 | n-C₄H₉ | 85 (C⟶N) | 176 (N⇌I) |
| 37 | n-C₆H₁₃ | -{O...O}- | 0 | F | 113 (C⟶N) | 174 (N⇌I) |
| 38 | n-C₄H₉ | — | 0 | —CH₂OCH₃ | −25 (C⟶I) | |
| 39 | n-C₅H₁₁ | — | 0 | —CH₂OCH₃ | 39 (C⟶I) | 9 (I⇌N) |
| 40 | n-C₄H₉ | -{H}- | 0 | —CH₂OCH₃ | 108 (C⟶S) | 112 (S⇌N) 196 (N⇌I) |

All of the compounds of formula (I) in accordance with this invention show weak negative dielectric anisotropy. Most of them are nematic liquid crystalline compounds, and some of them are compounds similar to liquid crystals. Accordingly, they can be used, for example in the form of a mixture with other nematic liquid crystalline compounds having negative or weakly positive dielectric anisotropy, as a material for dynamic scattering mode display cells. Furthermore, as a mixture with other nematic liquid crystalline compounds having strong positive dielectric anistropy, they can be used as a material for field effect mode display cells.

Typical examples of preferred nematic liquid crystalline compounds which can be used as mixtures with the compounds of general formula (I) include 4-substituted phenyl 4'-substituted benzoates, 4-substituted phenyl 4'-substituted cyclohexanecarboxylates, 4-substituted biphenyl 4'-substituted cyclohexanecarboxylates, 4-substituted phenyl 4'-(4"-substituted cyclohexanecarbonyloxy)benzoates, 4-substituted phenyl 4'-(4"-substituted cyclohexyl)benzoates, 4-substituted cyclohexyl 4-(4-substituted cyclohexyl)benzoates, 4',4"-substituted biphenyls, 4-substituted 4'-substituted phenylcyclohexanes, 4-substituted 4'-substituted terphenyls, 4-substituted 4'-biphenylcyclohexane, and 2-(4'-substituted phenyl)-5-substituted pyrimidines.

Table 2 summarizes the viscosities and Δn values (anisotropy of refractive index) measured of mixed crystals prepared from 75% by weight of matrix liquid crystals (A) now in widespread use as a nematic liquid crystalline material and 25% by weight of the compounds Nos. 1 to 5 of formula (I) respectively, and for comparison, of the matrix liquid crystals (A) themselves.

The matrix liquid crystals (A) are composed of 40% by weight of

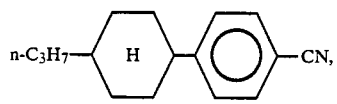

30% by weight of

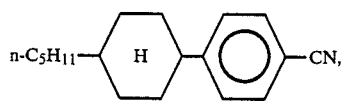

and
30% by weight of

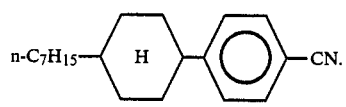

TABLE 2

|  | Viscosity at 20° C. (c.p.) | Δn (—) |
|---|---|---|
| (A) | 22.0 | 0.118 |
| (A) + No. 1 | 17.6 | 0.132 |
| (A) + No. 2 | 17.7 | 0.133 |
| (A) + No. 3 | 18.1 | 0.131 |
| (A) + No. 4 | 18.4 | 0.129 |
| (A) + No. 5 | 18.3 | 0.129 |

From the data presented in Table 2, it can be understood that the compounds Nos. 1 to 5 of formula (I) shown in Table 1 can reduce the viscosity of the matrix liquid crystals (A), and increase their refractive index anisotropy (Δn).

The characteristic properties of these compounds can also be demonstrated by the following experiment.

A compound of the following formula

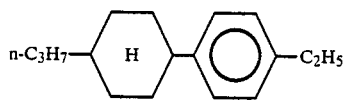
(a)

which is known to be an especially superior viscosity reducing agent for the production of fast-responsive liquid crystal display cells was mixed in varying proportions with the matrix liquid crystals (A) described above.

Likewise, compound No. 1 of this invention having the following formula

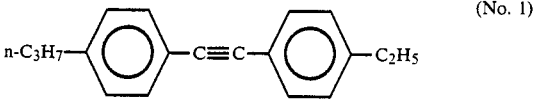
(No. 1)

was mixed in varying proportions with the matrix liquid crystals (A).

The viscosities and Δn values of the resulting mixed liquid crystals were measured.

FIG. 1 of the accompanying drawings is a graph drawn on the basis of the results of measurement and showing the relation between the viscosities and Δn values.

The results will demonstrate that while the known superior viscosity reducing agent reduces Δn, the compounds of formula (I) in accordance with this invention (Nos. 1 to 5 shown in Table 1) reduce the viscosity of liquid crystals and at the same time increase their Δn and thereby can greatly improve the response speed of the liquid crystals.

Table 3 summarizes the N-I points and Δn values (anisotropy of refractive index) of mixed liquid crystals composed of 90% by weight of matrix liquid crystals (B) shown below with 10% by weight of compounds Nos. 6 to 40 shown in Table 1 and for comparison, of the matrix liquid crystals (B). The matrix liquid crystals (B) are composed of
20% by weight of

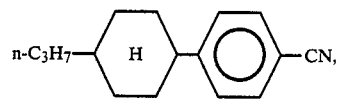

16% by weight of

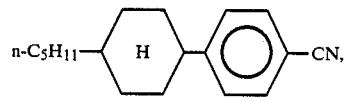

16% by weight of

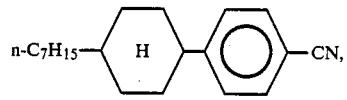

8% by weight of

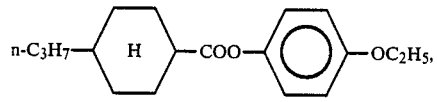

8% by weight of

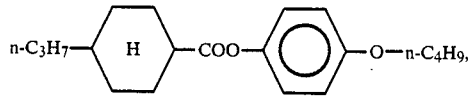

8% by weight of

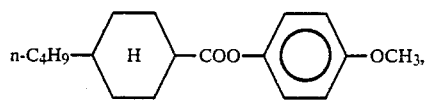

8% by weight of

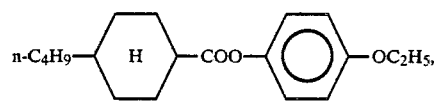

8% by weight of

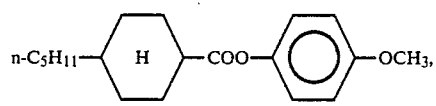

and
8% by weight of

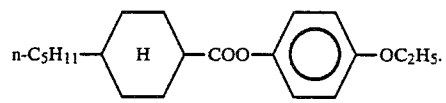

TABLE 3

| Mixed crystals | N-I point (°C.) | Δn (—) |
| --- | --- | --- |
| (A) | 54.0 | 0.0917 |
| (A) + No. 6 | 67.4 | 0.119 |
| (A) + No. 7 | 68.2 | 0.118 |
| (A) + No. 8 | 68.3 | 0.118 |
| (A) + No. 9 | 71.0 | 0.121 |
| (A) + No. 10 | 67.7 | 0.118 |
| (A) + No. 11 | 68.5 | 0.118 |
| (A) + No. 12 | 74.9 | 0.116 |
| (A) + No. 13 | 70.4 | 0.115 |
| (A) + No. 14 | 70.2 | 0.114 |
| (A) + No. 15 | 67.1 | 0.111 |
| (A) + No. 16 | 73.2 | 0.116 |
| (A) + No. 17 | 69.1 | 0.115 |
| (A) + No. 18 | 68.9 | 0.113 |
| (A) + No. 19 | 66.2 | 0.110 |
| (A) + No. 20 | 66.3 | 0.110 |
| (A) + No. 21 | 68.7 | 0.112 |
| (A) + No. 22 | 67.5 | 0.109 |
| (A) + No. 23 | 68.5 | 0.109 |
| (A) + No. 24 | 68.1 | 0.109 |
| (A) + No. 25 | 66.8 | 0.110 |
| (A) + No. 26 | 69.3 | 0.120 |
| (A) + No. 27 | 69.5 | 0.121 |
| (A) + No. 28 | 68.4 | 0.120 |
| (A) + No. 29 | 68.1 | 0.120 |
| (A) + No. 30 | 82.0 | 0.111 |
| (A) + No. 31 | 81.8 | 0.109 |
| (A) + No. 32 | 82.1 | 0.111 |
| (A) + No. 33 | 81.9 | 0.110 |
| (A) + No. 34 | 67.3 | 0.118 |
| (A) + No. 35 | 65.0 | 0.119 |
| (A) + No. 36 | 64.2 | 0.118 |
| (A) + No. 37 | 63.6 | 0.120 |
| (A) + No. 38 | — | 0.104 |
| (A) + No. 39 | — | 0.103 |
| (A) + No. 40 | — | 0.110 |

The data presented in Table 3 demonstrate that the compounds Nos. 6 to 40 shown in Table 1 increase the N-I point of the matrix liquid crystals (B) to a level sufficient for practical purposes and also greatly increase their Δn.

The characteristic properties of these compounds will also be demonstrated by the following comparative experiment.

Known compounds of the following formulae (b) to (i) which are similar in chemical structure to the compounds of formula (I) in accordance with this invention and are used to increase the N-I points of mixed liquid crystals were each mixed in various proportions with the matrix liquid crystals (B).

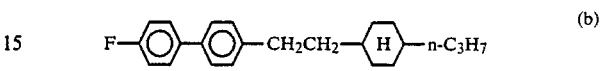
(b)

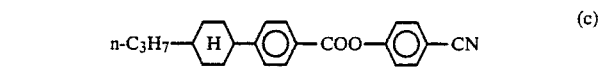
(c)

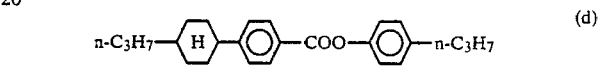
(d)

or

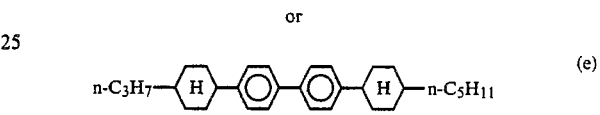
(e)

On the other hand, compounds of this invention structurally similar to the four known compounds shown above (Nos. 7, 13, 21 and 33) were each mixed in various proportions with the matrix liquid crystals (B).

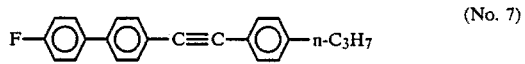
(No. 7)

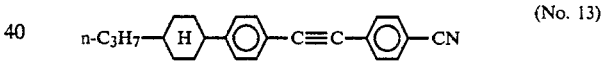
(No. 13)

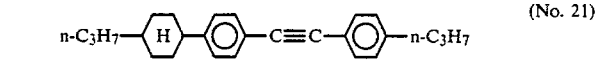
(No. 21)

or

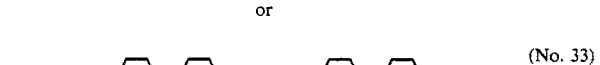
(No. 33)

The N-I points and Δn values of the resulting mixed liquid crystals were measured.

FIGS. 2, 4, 6 and 8 of the accompanying drawings are graphs drawn on the basis of the results of measurement and showing the relation between the N-I points and the amounts added.

FIGS. 3, 5, 7 and 9 of the accompanying drawings are graphs drawn on the basis of the results of measurement and showing the relation between Δn and the amounts added.

A comparative study of these graphs will show that as compared with the known compounds of formulae (b), (c), (d) and (e), the compounds of this invention Nos. 7, 13, 21 and 33 can greatly increase the N-I points and Δn values of the matrix liquid crystals.

The following Examples illustrate the present invention more specifically.

EXAMPLE 1

Anhydrous aluminum chloride (16 g; 0.120 mole) was added to 200 ml of carbon disulfide, and while heating the solution under reflux, a mixture of 10.6 g (0.100 mole) of ethylbenzene and 19.7 g (0.100 mole) of 4-n-propylphenylacetyl chloride was added dropwise to the solution. The mixture was heated under reflux for 1 hour, and carbon disulfide was evaporated. The product was added to ice water, and the mixture was stirred at 60° C. for 1 hour. After cooling, the product was extracted with toluene, washed with water and dried. Toluene was evaporated, and the residue was recrystallized from methanol to give 20 g (0.0752 mole) of a compound of the following formula.

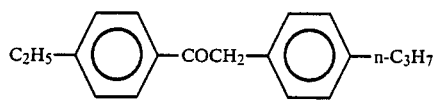

The compound was dissolved in 50 ml of anhydrous tetrahydrofuran (THF), and the solution was added dropwise to a mixed solution of 3.2 g (0.0840 mole) of lithium aluminum hydride and 120 ml of anhydrous THF to perform reaction at room temperature for 1 hour. To the solution were added 200 ml of 9% HCl and 200 ml of water. The product was extracted with toluene, washed with water and dried. Toluene was evaporated from the extract and the residue was dissolved in 300 ml of toluene. Potassium hydrogen sulfate (3 g; 0.0220 mole) was added to the solution, and the mixture was heated under reflux for 1 hour while removing water. After the reaction, the inorganic materials were separated by filtration and toluene was evaporated. Subsequent recrystallization from ethanol gave 15 g (0.0600 mole) of a compound of the following formula.

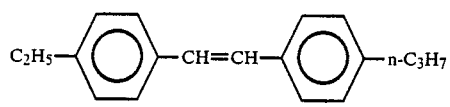

The resulting compound was dissolved in 200 ml of 1,1,2-trichloroethane, and at room temperature 9.6 g (0.0600 mole) of bromine was added dropwise to the solution to perform reaction for 1 hour. Methanol (150 ml) was added to the reaction solution, and the mixture was cooled. The precipitated crystals were collected by filtration, washed with methanol, and dried. The resulting compound was dissolved in 100 ml of N,N-dimethylformamide, and 14 g (0.0921 mole) of 1,5-diazabicyclo[5.4.0]undecene-5 was added. The mixture was heated under reflux for 2 hour. After cooling, dilute hydrochloric acid was added to render the reaction mixture acidic. It was then extracted with ethyl acetate, washed with water and dried, and the solvent was evaporated. Subsequent recrystallization from methanol gave 8.70 g (0.0351 mole) of a compound of the following formula.

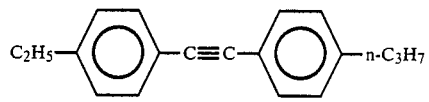

Yield: 46.7%.
Transition temperature: 51° C. (C→I).

EXAMPLE 2

A compound of the following formula was produced in the same way as in Example 1.

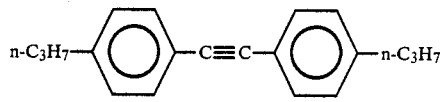

Yield: 43.5%.
Transition temperature: 73° C. (C→I).

EXAMPLE 3

A compound of the following formula was producd in the same way as in Example 1.

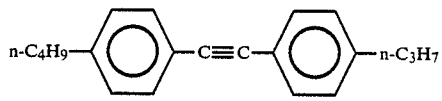

Yield: 45.3%.
Transition temperature:

| |
|---|
| 22° C. (C → I) |
| 15° C. (I ⇌ N) |

EXAMPLE 4

A compound of the following formula was produced in the same way as in Example 1.

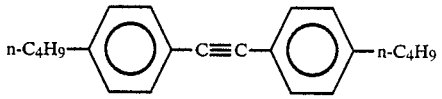

Yield: 45.1%.
Transition temperature: 41° C. (C→I).

EXAMPLE 5

A compound of the following formula was producd in the same way as in Example 1.

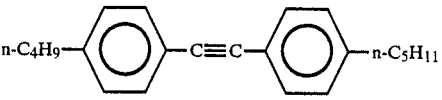

Yield: 45.4%.
Transition temperature:

| |
|---|
| 26° C. (C → I) |
| 21° C. (I ⇌ N) |

EXAMPLE 6

Anhydrous aluminum chloride (16.0 g; 0.120 mole) was added to 150 ml of carbon disulfide, and while heating the solution under reflux, a mixture of 17.2 g (0.100 mole) of fluorobiphenyl and 19.7 g (0.100 mole) of 4-n-propylphenylacetyl chloride was added dropwise to the solution. The mixture was heated under reflux for 1 hour, and carbon disulfide was evaporated. The product was added to ice water, and stirred at 60° C. for 1 hour. After cooling, the product was extracted with toluene, washed with water and dried. Toluene was evaporated, and subsequent recrystallization from ethanol-acetone gave 27 g (0.0813 mole) of a compound of the following formula.

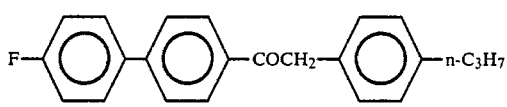

The resulting compound as crystals was gradually added to a mixed solution of 3.10 g (0.0813 mole) of aluminum lithium hydride and 100 ml of anhydrous THF to perform reaction at room temperature for 1 hour. Furthermore, 300 ml of 9% HCl and 300 ml of water were added. The mixture was then extracted with toluene, washed with water and dried. Toluene was evaporated from the extract, and the resulting crystals were dissolved in 300 ml of toluene. Furthermore, 2.7 g (0.0198 mole) of potassium hydrogen sulfate was added to the solution. The mixture was heated under reflux for 1 hour while removing water. After the reaction, the product was washed with water and dried. Toluene was evaporated, and the residue was recrystallized from ethanol-acetone to give 22 g (0.0701 mole) of a compound of the following formula.

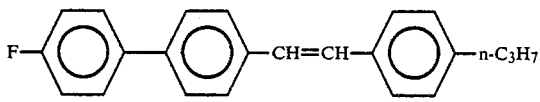

The resulting compound was dissolved in 250 ml of 1,1,2-trichloroethane, and while 11.2 g (0.0701 mole) of bromine was added dropwise to the solution at room temperature, the reaction was carried out for 1 hour. The precipitated crystals were collected by filtration, washed with methanol, and dried. The resulting compound was dissolved in 200 ml of N,N-dimethylformamide. To the solution was further added 20 g (0.132 mole) of 1,5-diazabicyclo[5.4.0]undecene-5, and the mixture was heated under reflux for 5 hours. After cooling, the product was extracted with toluene, washed with water and dried. Subsequent recrystallization from ethanol-acetone gave 10 g (0.0316 mole) of a compound of the following formula.

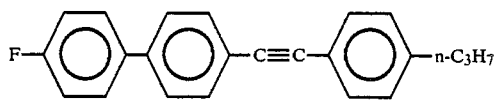

Yield: 31.6%.
Transition temperature:

| |
|---|
| 162° C. (C → N) |
| 202° C. (N ⇌ I) |

EXAMPLE 7

A compound of the following formula was produced in the same way as in Example 6.

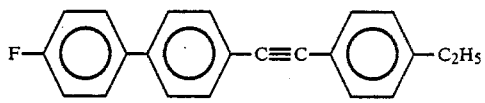

Yield: 30.7%.
Transition temperature:

| |
|---|
| 159° C. (C → N) |
| 193° C. (N ⇌ I) |

EXAMPLE 8

A compound of the following formula was produced in the same way as in Example 6.

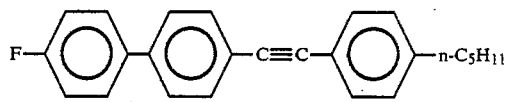

Yield: 32.2%.
Transition temperature:

| |
|---|
| 165° C. (C → N) |
| 204° C. (N ⇌ I) |

EXAMPLE 9

A compound of the following formula was produced in the same way as in Example 6.

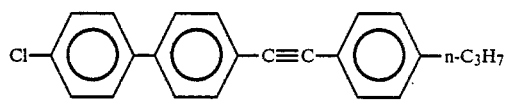

Yield: 31.4%.
Transition temperature:

| |
|---|
| 188° C. (C → N) |
| 230° C. (N ⇌ I) |

EXAMPLE 10

A compound of the following formula was produced in the same way as in Example 6.

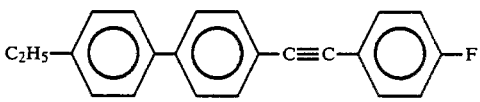

Yield: 34.3%.

Transition temperature:

| 150° C. (C → N) |
| --- |
| 196° C. (N ⇌ I) |

EXAMPLE 11

A compound of the following formula was produced in the same way as in Example 6.

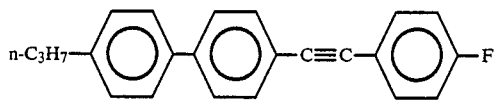

Yield: 32.8%.
Transition temperature:

| 150° C. (C → N) |
| --- |
| 207° C. (N ⇌ I) |

EXAMPLE 12

Anhydrous aluminum chloride (24.0 g; 0.180 mole) was added to 250 ml of carbon disulfide, and while heating the solution under reflux, a mixture of 30.3 g (0.15 mole) of trans-4-propyl-1-phenylcyclohexane and 35 g (0.15 mole) of 4-bromo-phenylacetyl chloride was added dropwise. The mixture was heated under reflux for 1 hour, and carbon disulfide was evaporated. The residue was added to ice water, and then stirred at 60° C. for 1 hour. After cooling, the product was extracted with toluene, washed with water, and dried. Toluene was evaporated, and the residue was recrystallized from ethanol-toluene (2:1) to give 35 g (0.088 mole) of a compound of the following formula.

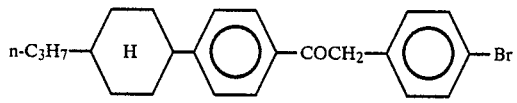

The resulting compound was dissolved in anhydrous THF, and the solution was added dropwise to a mixed solution of 4.00 g (0.105 mole) of aluminum lithium hydroxide and 150 ml of anhydrous THF. The reaction was carried out at room temperature for 2 hours. Then, 200 ml of 9% HCl and 200 ml of water were added, and the reaction mixture was extracted with toluene, washed with water and dried. Toluene was evaporated. The resulting crystals were dissolved in 300 ml of toluene, and 2.80 g (0.0206 mole) of potassium hydrogen sulfate was added. While water was removed by a decanter, the mixture was heated under reflux for 1 hour. After the reaction, the inorganic materials were separated by filtration. The filtrate containing the product was recrystallized to give 26.8 g (0.07 mole) of a compound of the following formula.

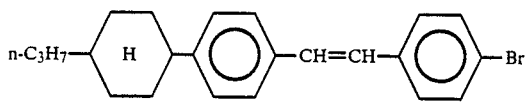

The resulting compound was dissolved in 150 ml of 1,1,2-trichloroethane, and reacted for 1.5 hours while adding dropwise 12.3 g (0.077 mole) of bromine at room temperature. The precipitated crystals were collected by filtration, washed with methanol, and dried. The resulting compound was dissolved in 250 ml of N,N-dimethylformamide, and 11.7 g (0.077 mole) of 1,5-azabicyclo[5.4.0]undecene-5 was added. The mixture was heated under reflux for 4 hours. After cooling, water was added. The precipitated crystals were collected by filtration, washed with methanol, and dried to give 18.9 g (0.0496 mole) of a compound of the following formula.

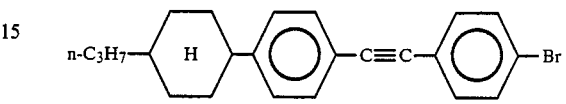

Yield: 33.1%.
Transition temperature:

| 155° C. (C → N) |
| --- |
| 211° C. (N ⇌ I) |

EXAMPLE 13

3.81 g (0.0100 mole) of the tolan derivative obtained in Example 12 was dissolved in 70 ml of N,N-dimethylformamide, and 1.35 g (0.015 mole) of cuprous cyanide was added. The mixture was heated under reflux for 12 hours. After cooling, a hydrochloric acid solution of ferric chloride was added, and the mixture was stirred for 0.5 hour. The reaction mixture was extracted with ether, washed with water, and dried. Subsequent recrystallization from ethanol-toluene (1:2) gave 2.30 g (0.00703 mole) of a compound of the following formula.

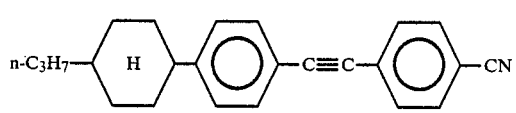

Yield: 23.3%.
Transition temperature:

| 153° C. (C → N) |
| --- |
| 265° C. (N ⇌ I) |

EXAMPLE 14

A compound of the following formula was produced in the same way as in Example 12.

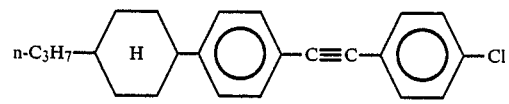

Yield: 34.2%.
Transition temperature:

| 141° C. (C → N) |
| --- |

-continued

| 219° C. (N ⇌ I) |
|---|

EXAMPLE 15

A compound of the following formula was produced in the same way as in Example 12.

n-C₃H₇—⟨H⟩—⟨O⟩—C≡C—⟨O⟩—F

Yield: 32.7%.
Transition temperature:

| 90° C. (C → N) |
|---|
| 189° C. (N ⇌ I) |

EXAMPLE 16

A compound of the following formula was produced in the same way as in Example 12.

C₂H₅—⟨H⟩—⟨O⟩—C≡C—⟨O⟩—CN

Yield: 22.7%
Transition temperature:

| 135° C. (C → N) |
|---|
| 250° C. (N ⇌ I) |

EXAMPLE 17

A compound of the following formula was produced in the same way as in Example 12.

C₂H₅—⟨H⟩—⟨O⟩—C≡C—⟨O⟩—Br

Yield: 33.8%.
Transition temperature:

| 136° C. (C → N) |
|---|
| 209° C. (N ⇌ I) |

EXAMPLE 18

A compound of the following formula was produced in the same way as in Example 12.

C₂H₅—⟨H⟩—⟨O⟩—C≡C—⟨O⟩—Cl

Yield: 34.7%.
Transition temperature:

| 124° C. (C → N) |
|---|
| 207° C. (N ⇌ I) |

EXAMPLE 19

A compound of the following formula was produced in the same way as in Example 12.

C₂H₅—⟨H⟩—⟨O⟩—C≡C—⟨O⟩—F

Yield: 32.2%.
Transition temperature:

| 78° C. (C → N) |
|---|
| 179° C. (N ⇌ I) |

EXAMPLE 20

Anhydrous aluminum chloride (24.0 g; 0.180 mole) was added to 200 ml of carbon disulfide, and while heating the solution under reflux, a solution composed of 28.2 g (0.150 mole) of trans-4-ethyl-1-phenylcyclohexane, 29.5 g (0.150 mole) of 4-n-propylphenylacetyl chloride and 50 ml of carbon disulfide was gradually added dropwise. After the addition, the mixture was refluxed for 1 hour. The reaction mixture was cooled, added to ice water and stirred at 60° C. for 1 hour. Carbon disulfide was evaporated, and the residue was extracted with toluene, washed with water, and dried over anhydrous sodium sulfate. Toluene was evaporated, and the residue was recrystallized from ethanol-toluene (2:1) to give 38.1 g (0.109 mole) of a compound of the following formula.

C₂H₅—⟨H⟩—⟨O⟩—COCH₂—⟨O⟩—n-C₃H₇

The resulting compound was dissolved in anhydrous THF, and the solution was added dropwise to a mixed solution composed of 4.96 g (0.131 mole) of aluminum lithium hydride and 150 ml of anhydrous THF. The mixture was refluxed for 2 hours, and 250 ml of 9% hydrochloric acid and 250 ml of water were added dropwise. The reaction mixture was extracted with toluene, washed with water, and dried over anhydrous sodium sulfate. The solvent was evaporated to give a crude product of the following formula.

C₂H₅—⟨H⟩—⟨O⟩—CHCH₂—⟨O⟩—n-C₃H₇
                    |
                    OH

The crude product was dissolved in 300 ml of toluene, and 3.56 g (0.0262 mole) of potassium hydrogen sulfate was added. With refluxing, the dehydration reaction was carried out, and water was removed by a decanter. After the reaction, the reaction product was washed with water and dried. Toluene was evaporated, and the residue was recrystallized from ethanol-toluene (1:2) to give 27.5 g (0.0828 mole) of a compound of the following formula.

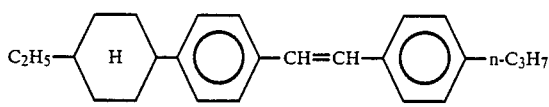

The resulting compound was dissolved in 200 ml of 1,1,2-trichloroethane, and with stirring at 10° C., 14.6 g (0.0913 mole) of bromine was added dropwise, and the reaction was carried out for 2 hours. The reaction mixture was cooled. The precipitated crystals were collected by filtration, washed with methanol, and dried. The resulting compound was dissolved in 250 ml of N,N-dimethylformamide, and 13.8 g (0.0908 mole) of 1,5-diazabicyclo[5.4.0]undecene-5 was added. The mixture was refluxed for 5 hours. After the reaction, the reaction mixture was cooled, and water was added. The precipitated crystals were collected by filtration, washed with methanol, and dried. The product was recrystallized from ethanol-toluene (1:2) to give 17.3 g (0.0524 mole) of a compound of the following formula.

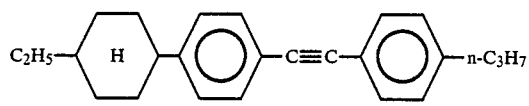

Yield: 34.5%.
Transition temperature:

| |
|---|
| 86° C. (C → N) |
| 189° C. (N ⇌ I) |

EXAMPLE 21

A compound of the following formula was produced in the same way as in Example 20.

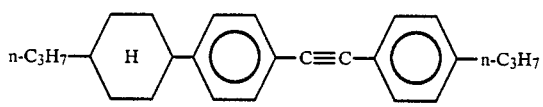

Yield: 35.8%.
Transition temperature:

| |
|---|
| 96° C. (C → N) |
| 213° C. (N ⇌ I) |

EXAMPLE 22

A compound of the following formula was produced in the same way as in Example 20.

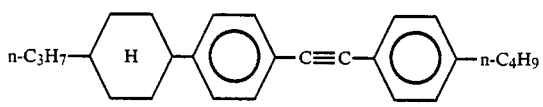

Yield: 35.1%.

Transition temperature:

| |
|---|
| 87° C. (C → N) |
| 201° C. (N ⇌ I) |

EXAMPLE 23

A compound of the following formula was produced in the same way as in Example 20.

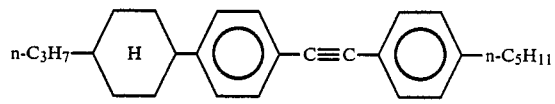

Yield: 36.4%.
Transition temperature:

| |
|---|
| 98° C. (C → N) |
| 209° C. (N ⇌ I) |

EXAMPLE 24

A compound of the following formula was produced in the same way as in Example 20.

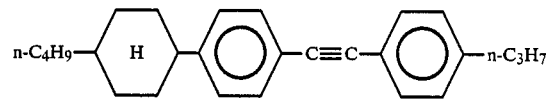

Yield: 34.0%.
Transition temperature:

| |
|---|
| 89° C. (C → N) |
| 207° C. (N ⇌ I) |

EXAMPLE 25

A compound of the following formula was produced in the same way as in Example 20.

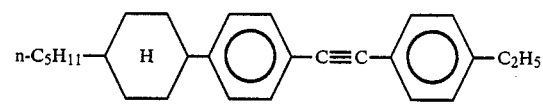

Yield: 32.7%.
Transition temperature:

| |
|---|
| 91° C. (C → N) |
| 192° C. (N ⇌ I) |

EXAMPLE 26

A compound of the following formula was produced in the same way as in Example 20.

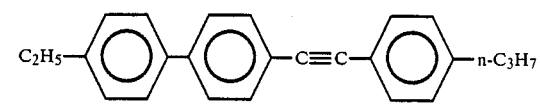

Yield: 36.9%.
Transition temperature:

| |
|---|
| 163° C. (C → N) |
| 221° C. (N ⇌ I) |

EXAMPLE 27

A compound of the following formula was produced in the same way as in Example 20.

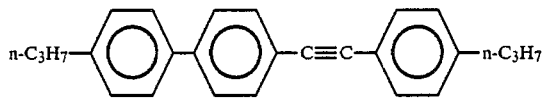

Yield: 37.4%.
Transition temperature:

| |
|---|
| 164° C. (C → N) |
| 230° C. (N ⇌ I) |

EXAMPLE 28

A compound of the following formula was produced in the same way as in Example 20.

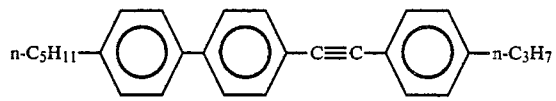

Yield: 37.1%.
Transition temperature:

| |
|---|
| 160° C. (C → N) |
| 211° C. (N ⇌ I) |

EXAMPLE 29

A compound of the following formula was produced in the same way as in Example 20.

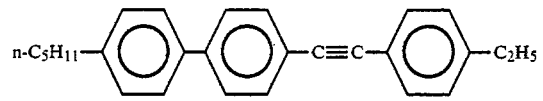

Yield: 36.6%.
Transition temperature:

| |
|---|
| 157° C. (C → N) |
| 206° C. (N ⇌ I) |

EXAMPLE 30

To 100 ml of carbon disulfide was added 9 g (0.0680 mole) of anhydrous aluminum chloride, and while heating the solution under reflux, a mixture of 9.4 g (0.0500 mole) of trans-4-ethyl-1-phenylcyclohexane and 14 g (0.0500 mole) of trans-4-n-propylcyclohexylphenylacetyl chloride was added dropwise to the solution. The mixture was heated under reflux for 1 hour, and carbon disulfide was evaporated. The product was added to ice water, and stirred at 60° C. for 1 hour. After cooling, the reaction product was extracted with toluene, washed with water and dried. Toluene was evaporated, and the residue was recrystallized from ethanol to give 18 g (0.0420 mole) of a compound of the following formula.

The resulting compound as crystals was gradually added to a mixture of 1.6 g (0.0420 mole) of aluminum lithium hydride and 80 ml of anhydrous THF, and the reaction was carried out at room temperature for 1 hour. To the reaction solution were added 150 ml of 9% HCl and 150 ml of water. The mixture was extracted with toluene, washed with water, and dried. Toluene was evaporated from the extract. The resulting crystals were dissolved in 300 ml of toluene, and 1.5 g (0.0110 mole) of potassium hydrogen sulfate was added to the solution. While removing water, the mixture was heated under reflux for 1 hour. After the reaction, the inorganic materials were separated by filtration, and the residue was recrystallized to give 14.4 g (0.0350 mole) of a compound of the following formula.

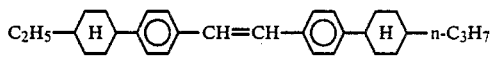

The resulting compound was dissolved in 250 ml of 1,1,2-trichloroethane, and 5.6 g (0.0350 mole) of bromine was added dropwise at room temperature. The reaction was thus carried out for 1 hour. The precipitated crystals were collected by filtration, washed with methanol, and dried. The resulting compound was dissolved in 120 ml of N,N-dimethylformamide. To the solution was further added 14 g (0.0921 mole) of 1,5-diazabicyclo[5.4.0]undecene-5, and the mixture was heated under reflux for 3 hours. After cooling, the reaction product was extracted with toluene, washed with water, and dried. Subsequent recrystallization from ethanol-acetone gave 8 g (0.0200 mole) of a compound of the following compound.

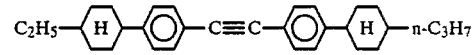

Yield: 40.0%.
Transition temperature:

| |
|---|
| 194° C. (C → N) |
| above 300° C. (N ⇌ I) |

EXAMPLE 31

A compound of the following formula was produced in the same way as in Example 30.

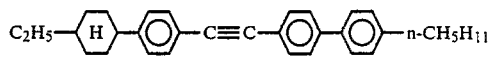

Yield: 37.5%.
Transition temperature:

| 210° C. (C → N) |
| --- |
| above 300° C. (N ⇌ I) |

EXAMPLE 32

A compound of the following formula was produced in the same way as in Example 30.

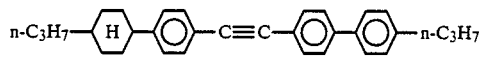

Yield: 34.7%.
Transition temperature:

| 185° C. (C → N) |
| --- |
| above 300° C. (N ⇌ I) |

EXAMPLE 33

A compound of the following formula was produced in the same way as in Example 30.

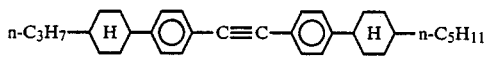

Yield: 36.4%.
Transition temperature:

| 202° C. (C → N) |
| --- |
| above 300° C. (N ⇌ I) |

EXAMPLE 34

A mixture of 5.4 g (0.048 mole) of 2-n-propyl-1,3-propanediol and 11.2 g (0.048 mole) of p-iodobenzaldehyde was dissolved in 100 ml of toluene, and a catalytic amount of p-toluenesulfonic acid was added. The mixture was heated under reflux for 2 hours. After the reaction, the toluene layer was washed with water and dried. Toluene was evaporated under reduced pressure, and the residue was recrystallized from methanol to give 13 g (0.039 mole) of a compound of the following formula.

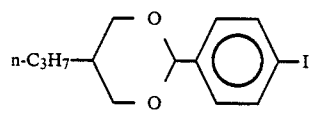

3.3 g (0.010 mole) of this compound was dissolved in 30 ml of N,N-dimethylformamide, and 3.3 mg (0.0047 mole) of bis(tripheylphosphine)palladium (II) chloride, 17 mg (0.088 mole) of cuprous iodide and 0.7 g (0.091 mole) of diethylamine were added. With stirring, 1.6 g (0.010 mole) of 4-n-butylphenylacetylene was further added. The reaction was carried out at room temperature for 1 hour. After the reaction, 30 ml of 9% hydrochloric acid was added, and the reaction product was extracted with toluene. The extract was washed with water, and dried, and toluene was evaporated under reduced pressure. The product was recrystallized from ethanol to give 2.6 g (0.0072 mole) of a compound of the following formula.

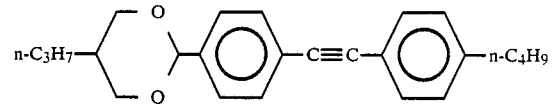

Yield: 72%.
Transition temperature:

| 83° C. (C → N) |
| --- |
| 195° C. (N ⇌ I) |

EXAMPLE 35

A compound of the following formula was produced in the same way as in Example 34.

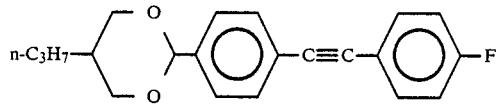

Yield: 64%.
Transition temperature:

| 118° C. (C → N) |
| --- |
| 178° C. (N ⇌ I) |

EXAMPLE 36

A compound of the following formula was produced in the same way as in Example 34.

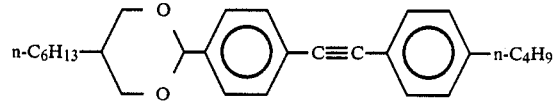

Yield: 68%.
Transition temperature:

| 85° C. (C → N) |
| --- |
| 176° C. (N ⇌ I) |

EXAMPLE 37

A compound of the following formula was produced in the same way as in Example 34.

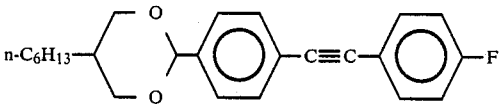

Yield: 61%.
Transition temperature:

| 113° C. (C → N) |
| --- |
| 174° C. (N ⇌ I) |

EXAMPLE 38

Periodic acid (7.1 g; 0.0310 mole) and 33.7 g (0.138 mole) of iodine were dissolved in a mixed solvent composed of 122 ml of acetic acid, 23 ml of water and 15 ml of carbon tetrachloride, and 32.3 g (0.265 mole) of methyl benzyl ether was added. The mixture was heated under reflux for 20 hours. After the reaction, a solution of 32 g (0.300 mole) of sodium hydrogen sulfite in 200 ml of water was added. The reaction product was extracted with ether. The extract was washed with water and dried. Ether was evaporated, and the residue was distilled under reduced pressure to give 45 g (0.182 mole) of a compound of the following formula.

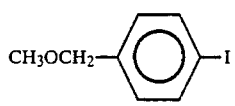

A portion (7.5 g; 0.0300 mole) of the resulting compound was dissolved in 50 ml of N,N-dimethylformamide, and 10 mg (0.0142 mmole) of bis(triphenylphosphine)palladium (II) chloride, 50 mg (0.263 mmole) of cuprous iodide and 2 g (0.274 mole) of diethylamine were added to the solution. With stirring, 5.2 g (0.0300 mole) of 4-n-pentylphenylacetylene was added, and the reaction was carried out at room temperature for 1 hour. After the reaction, 50 ml of 9% hydrochloric acid was added, and the reaction product was extracted with toluene. The extract was washed with water and dried. Toluene was evaporated, and the residue was recrystallized from methanol to give 4 g of a compound of the following formula.

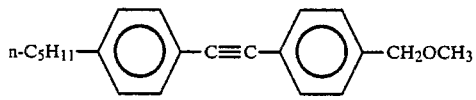

Yield: 46%.
Transition temperature:

| |
|---|
| 39° C. (C → I) |
| 9° C. (I ⇌ N) |

EXAMPLE 39

A compound of the following formula was produced in the same way as in Example 38.

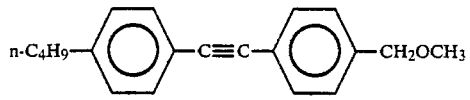

Yield: 42%.
Transition temperature: −25° C. (C→I).

EXAMPLE 40

A compound of the following formula was produced in the same way as in Example 38.

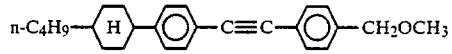

Yield: 40%.
Transition temperature:

| |
|---|
| 108° C. (C → S) |
| 112° C. (S ⇌ N) |
| 196° C. (N ⇌ I) |

What is claimed is:

1. A mixed liquid crystalline composition exhibiting a nematic liquid crystal phase and low viscosity, said composition comprising a matrix liquid crystal component and at least one compound which is represented by the general formula

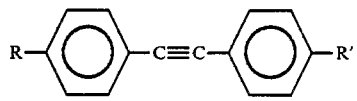

wherein R and R', independently from each other, represent a linear alkyl group having 1 to 5 carbon atoms, and the sum of the number of carbon atoms of R and R' is 3 to 7 in an amount effective to reduce the viscosity of the matrix liquid crystal component.

2. The composition of claim 1 wherein R is n—$C_3H_7$— and R' is $C_2H_5$—.
3. The composition of claim 1 wherein R is n—$C_3H_7$— and R' is n—$C_3H_7$—.
4. The composition of claim 1 wherein R is n—$C_3H_7$— and R' is n—$C_4H_9$—.
5. The composition of claim 1 wherein the matrix liquid crystal component comprises a mixture of at least two compounds selected from the group consisting of 4-substituted phenyl 4'-substituted benzoates, 4-substituted phenyl 4'-substituted cyclohexanecarboxylates, 4-substituted biphenyl 4'-substituted cyclohexanecarboxylates, 4-substituted phenyl 4'-(4''-substituted cyclohexanecarbonyloxy)benzoates, 4-substituted phenyl 4'-(4''-substituted cyclohexyl)benzoates, 4-substituted cyclohexyl 4'-(4''-substituted cyclohexyl)benzoates, 4-substituted 4'-substituted biphenyls, 4-substituted 4'-substituted phenylcyclohexanes, 4-substituted 4'-substituted terphenyls, 4-substituted 4'biphenylcyclohexanes, and 2-(4'-substituted phenyl)-5-substituted pyrimidines.
6. The composition of claim 1 wherein the matrix liquid crystal component comprises a mixture of compounds of the formula:

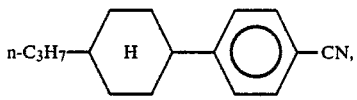

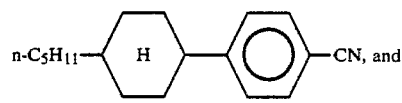

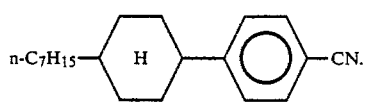

* * * * *

UNITED STATES PATENT AND TRADEMARK OFFICE
CERTIFICATE OF CORRECTION

PATENT NO. : 4,726,910

DATED : February 23, 1988

INVENTOR(S) : HARUYOSHI TAKATSU ET AL.

It is certified that error appears in the above-identified patent and that said Letters Patent is hereby corrected as shown below:

On the cover page of the patent under the heading
"Foreign Application Priority Datd', "59-261413"
(second occurrence) should read --59-261414--.

Signed and Sealed this

Twelfth Day of July, 1988

Attest:

DONALD J. QUIGG

Attesting Officer

Commissioner of Patents and Trademarks